(12) United States Patent
Uitenbroek et al.

(10) Patent No.: US 6,982,231 B1
(45) Date of Patent: Jan. 3, 2006

(54) ELASTOMERIC, BREATHABLE LAMINATE WITH ENHANCED BREATHABILITY UPON EXTENSION

(75) Inventors: Duane Girard Uitenbroek, Little Chute, WI (US); Susan Elaine Shawver, Roswell, GA (US); Paul Windsor Estey, Cumming, GA (US); Cindy Janja Blackstock, Cumming, GA (US); William Bela Haffner, Ball Ground, GA (US); Glynis Allicia Walton, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 841 days.

(21) Appl. No.: 09/698,595

(22) Filed: Oct. 27, 2000

(51) Int. Cl.
 *B32B 27/12* (2006.01)
(52) U.S. Cl. .................. 442/394; 442/328; 442/329; 442/417; 264/288.4; 264/288.8; 264/290.5; 264/291
(58) Field of Classification Search .................. 442/77, 442/172, 175, 328, 329, 394, 417; 264/288.4, 264/288.8, 290.5, 291
See application file for complete search history.

(56) References Cited

U.S. PATENT DOCUMENTS

| 3,338,992 | A | 8/1967 | Kinney |
| 3,341,394 | A | 9/1967 | Kinney |
| 3,502,538 | A | 3/1970 | Petersen |
| 3,502,763 | A | 3/1970 | Hartmann |
| 3,542,615 | A | 11/1970 | Dobo et al. |
| 3,692,618 | A | 9/1972 | Dorschner et al. |
| 3,802,817 | A | 4/1974 | Matsuki et al. |
| 3,849,241 | A | 11/1974 | Butin et al. |
| 4,100,324 | A | 7/1978 | Anderson et al. |
| 4,340,563 | A | 7/1982 | Appel et al. |
| 4,543,099 | A | 9/1985 | Bunnelle et al. |
| 4,606,964 | A | 8/1986 | Wideman |
| 4,640,726 | A | 2/1987 | Sallee et al. |
| 4,687,477 | A | 8/1987 | Suzuki et al. |
| 4,720,415 | A | 1/1988 | Vander Wielen et al. |
| 4,756,709 | A | 7/1988 | Stevens |
| 4,801,485 | A | 1/1989 | Sallee et al. |
| 4,829,096 | A * | 5/1989 | Kitamura et al. ............. 521/79 |
| 4,863,779 | A | 9/1989 | Daponte |
| 4,908,247 | A | 3/1990 | Baird et al. |
| 4,938,757 | A | 7/1990 | Van Gompel et al. |
| 4,981,747 | A | 1/1991 | Morman |
| 5,036,551 | A * | 8/1991 | Dailey et al. ................... 2/167 |
| 5,114,781 | A | 5/1992 | Morman |

(Continued)

FOREIGN PATENT DOCUMENTS

EP 0 236 032 12/1991

(Continued)

OTHER PUBLICATIONS

S.J. Kadolph & A.L. Langford : *Textiles*, Eighth Edition, © 1998 by Prentice-Hall Inc, no month.

*Primary Examiner*—Elizabeth M. Cole
*Assistant Examiner*—Andrew T. Piziali
(74) *Attorney, Agent, or Firm*—Pauley Petersen & Erickson

(57) ABSTRACT

An elastomeric, breathable laminate having enhanced breathability is formed by bonding a breathable, microporous, extendible/elastic film to a nonwoven facing material. The facing material can be necked to impart cross-directional stretchability. Once the film and the facing material are bonded together, the resulting laminate is stretched in one or more areas to impart higher breathability to selected areas of the laminate. The breathable laminate with enhanced breathability is particularly useful as an outer cover for diapers and other personal care products.

32 Claims, 5 Drawing Sheets

U.S. PATENT DOCUMENTS

| | | |
|---|---|---|
| 5,143,679 A | 9/1992 | Weber et al. |
| 5,156,793 A | 10/1992 | Buell et al. |
| 5,167,897 A | 12/1992 | Weber et al. |
| 5,171,388 A | 12/1992 | Hoffman et al. |
| 5,204,429 A | 4/1993 | Kaminsky et al. |
| 5,226,992 A | 7/1993 | Morman |
| 5,244,482 A | 9/1993 | Hassenboehler, Jr. et al. |
| 5,259,902 A | 11/1993 | Muckenfuhs |
| 5,272,236 A | 12/1993 | Lai et al. |
| 5,278,272 A | 1/1994 | Lai et al. |
| 5,300,365 A | 4/1994 | Ogale |
| 5,336,545 A | 8/1994 | Morman |
| 5,354,400 A | 10/1994 | Lavash et al. |
| 5,374,696 A | 12/1994 | Rosen et al. |
| 5,385,775 A | 1/1995 | Wright |
| 5,397,316 A | 3/1995 | LaVon et al. |
| 5,451,450 A | 9/1995 | Erderly et al. |
| 5,472,775 A | 12/1995 | Obijeski et al. |
| 5,492,753 A | 2/1996 | Levy et al. |
| 5,496,429 A | 3/1996 | Hasse et al. |
| 5,514,470 A | 5/1996 | Haffner et al. |
| 5,527,302 A | 6/1996 | Endres et al. |
| 5,539,124 A | 7/1996 | Etherton et al. |
| 5,554,143 A | 9/1996 | Roe et al. |
| 5,554,144 A | 9/1996 | Roe et al. |
| 5,554,145 A | 9/1996 | Roe et al. |
| 5,554,775 A | 9/1996 | Krishnamurti et al. |
| 5,556,394 A | 9/1996 | Roe et al. |
| 5,556,504 A | 9/1996 | Rajala et al. |
| 5,560,878 A | 10/1996 | Dragoo et al. |
| 5,569,232 A | 10/1996 | Roe et al. |
| 5,569,234 A | 10/1996 | Buell et al. |
| 5,582,903 A | 12/1996 | Levy et al. |
| 5,587,225 A | 12/1996 | Griesbach et al. |
| 5,611,790 A | 3/1997 | Osborn, III et al. |
| 5,615,460 A | 4/1997 | Weirich et al. |
| 5,624,422 A | 4/1997 | Allen |
| 5,624,427 A | 4/1997 | Bergman |
| 5,624,729 A | 4/1997 | Cohen et al. |
| 5,628,741 A | 5/1997 | Buell et al. |
| 5,628,856 A | 5/1997 | Dobrin et al. |
| 5,635,290 A | 6/1997 | Stopper et al. |
| 5,643,396 A | 7/1997 | Rajala et al. |
| 5,645,672 A | 7/1997 | Dobrin |
| 5,658,269 A | 8/1997 | Osborn, III et al. |
| 5,660,657 A | 8/1997 | Rajala et al. |
| 5,674,212 A | 10/1997 | Osborn, III et al. |
| 5,683,375 A | 11/1997 | Osborn, III et al. |
| 5,690,627 A | 11/1997 | Clear et al. |
| 5,695,868 A | 12/1997 | McCormack |
| 5,702,382 A | 12/1997 | Osborn, III et al. |
| 5,713,884 A | 2/1998 | Osborn, III et al. |
| 5,716,478 A | 2/1998 | Boothe et al. |
| 5,749,866 A | 5/1998 | Roe et al. |
| 5,749,989 A | 5/1998 | Linman et al. |
| 5,759,340 A | 6/1998 | Boothe et al. |
| H01750 H * | 9/1998 | Dobrin ...................... 604/383 |
| 5,843,056 A | 12/1998 | Good et al. |
| 5,855,999 A | 1/1999 | McCormack |
| 5,883,028 A | 3/1999 | Morman et al. |
| 5,916,663 A | 6/1999 | Chappell et al. |
| 5,921,973 A | 7/1999 | Newkirk et al. |
| 5,932,497 A | 8/1999 | Morman et al. |
| 6,004,306 A | 12/1999 | Robles et al. |
| 6,045,900 A | 4/2000 | Haffner et al. |
| 6,072,005 A | 6/2000 | Kobylivker et al. |
| 6,129,720 A | 10/2000 | Blenke et al. |
| 6,197,404 B1 | 3/2001 | Varona |
| 6,479,154 B1 | 11/2002 | Walton et al. |

FOREIGN PATENT DOCUMENTS

| | | |
|---|---|---|
| EP | 0 386 816 | 4/1994 |
| EP | 0 400 111 | 8/1994 |
| EP | 0 451 705 | 8/1994 |
| EP | 0 630 630 | 12/1994 |
| EP | 0 630 631 | 12/1994 |
| EP | 0 630 632 | 12/1994 |
| EP | 0 420 256 | 5/1995 |
| EP | 0 707 106 | 4/1996 |
| EP | 0 433 951 | 8/1996 |
| EP | 0 552 345 | 9/1996 |
| EP | 0 630 221 | 4/1997 |
| EP | 0 409 315 | 5/1997 |
| EP | 0 820 747 | 1/1998 |
| EP | 0 602 613 | 6/1998 |
| EP | 0 651 629 | 6/1998 |
| EP | 0 659 117 | 6/1998 |
| EP | 890 350 | 1/1999 |
| WO | 93/01785 | 2/1993 |
| WO | 98/17648 | 9/1993 |
| WO | 94/02094 | 2/1994 |
| WO | 96/16625 | 6/1996 |
| WO | 96/18367 | 6/1996 |
| WO | 97/36566 | 10/1997 |
| WO | 98/29246 | 7/1998 |
| WO | 99/32272 | 7/1999 |
| WO | WO 99/33426 | 7/1999 |
| WO | 01/82849 | 11/2001 |

* cited by examiner

ELASTOMERIC, BREATHABLE LAMINATE WITH ENHANCED BREATHABILITY UPON EXTENSION

FIELD OF THE INVENTION

This invention is directed to a breathable laminate configured to selectively enhance breathability in target areas.

BACKGROUND OF THE INVENTION

Breathable materials, such as breathable films, typically block the passage of particulate matter, water and other liquids while allowing water vapor and air to pass through the material. Thus, breathable materials are particularly suitable for use in garments and personal care products, thereby allowing moisture trapped beneath the fabric to escape as water vapor. Garments using breathable materials are generally more comfortable to wear since the migration of water vapor through the fabric helps to reduce and/or eliminate discomfort resulting from excess moisture trapped against the skin. Furthermore, the reduction of excess moisture leads to reduced relative humidity and temperature within the garment in comparison to such garments made of non-breathable films and laminates.

One example of a breathable material is a microporous film. This type of film is typically filled with particles or other matter and then crushed or stretched to form a fine pore network of micropores of a size and/or frequency to impart the desired level of breathability to the fabric. The microporous film can be laminated to a nonwoven web to create a laminate that takes advantage of the strength and integrity of the nonwoven web and the barrier properties of the stretched film. One example of such a laminate is disclosed in U.S. Pat. No. 6,045,900 issued to Haffner, et al.

Breathable laminates, including a layer of breathable film and one or more layers of other materials, are often not breathable enough, thereby resulting in excess vapor retention within the garment, personal care product, or other application made of the breathable laminate. In diapers and other pant-like absorbent articles, liquid can accumulate in the crotch region. When this happens, heat from the wearer's body can cause the space between garment and the wearer to become saturated with water vapor, facilitating the occurrence of diaper rashes and other skin irritations. The most effective way to vent the water vapor is through other regions of the garment which are not affected by the pool of liquid in the crotch.

There is a need or desire for a breathable laminate having enhanced breathability.

SUMMARY OF THE INVENTION

The present invention is directed to a microporous, extendible/elastic material having enhanced breathability. More particularly, the breathability of the material is increased in target zones of the material. The material is a laminate formed from a breathable, elastic, microporous film laminated to a nonwoven facing material. The nonwoven facing material can be necked to impart cross directional stretch. Target zones of higher breathability can be created by stretching the laminate in the target areas. The laminate is particularly useful as an outer cover for diapers and other personal care products.

The film can be a microporous film made of any elastomeric polymer. Suitable films can deliver breathability, expressed as water vapor transmission rate (WVTR), in a range of about 1,000 to 30,000 grams/m$^2$-24 hours using the Mocon WVTR test procedure described below. The targeted zones of high breathability can have a WVTR at least 10% greater than the remainder of the material. Suitable films include microporous films which contain an amorphous polymer and a filler.

The necked nonwoven facing material is extensible at least in the cross direction. Cross direction stretchability is achieved through necking the nonwoven material in the machine direction. Materials having machine direction stretchability can be used to impart machine direction stretchability to the resulting laminate. The film and the nonwoven facing material can be adhesively bonded together.

With the foregoing in mind, it is a feature and advantage of the invention to provide a breathable laminate having targeted zones of high breathability;

It is also a feature and advantage of the invention to provide an improved breathable laminate useful in a wide variety of diaper outer covers, other personal care products, surgical gowns, and other breathable applications.

The foregoing and other features and advantages of the invention will become further apparent from the following detailed description of the presently preferred embodiments, read in conjunction with the examples and drawings.

Definitions

Figure 1:
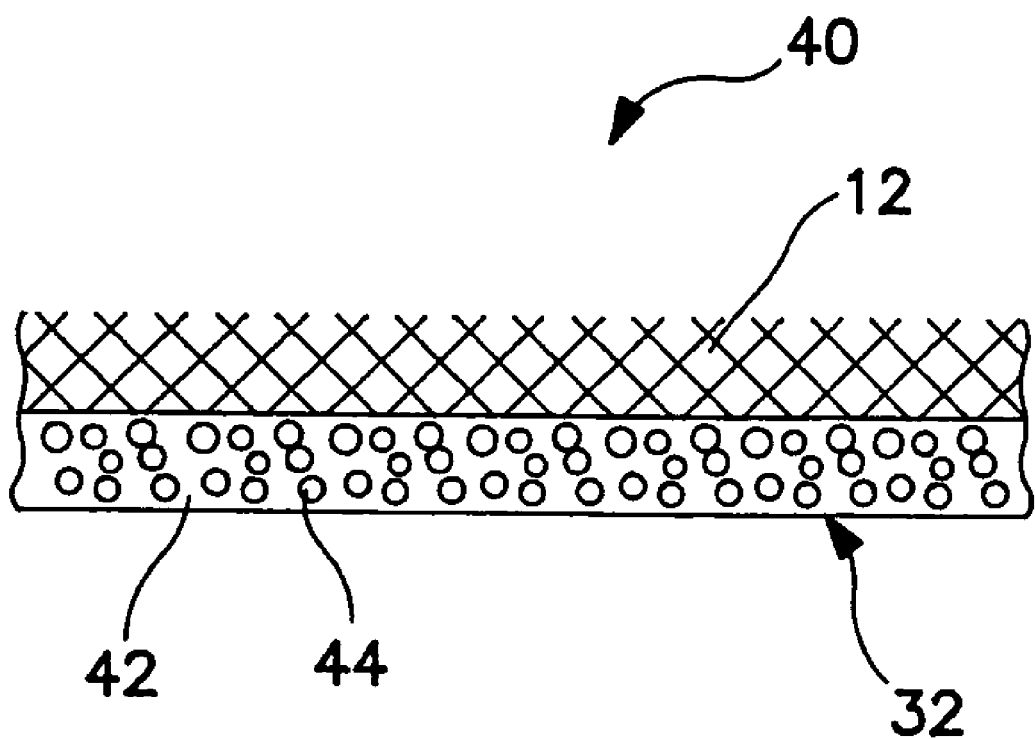
FIG. 1 is a cross-sectional view of a breathable laminate of the present invention.

Within the context of this specification, each term or phrase below will include the following meaning or meanings.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Cross direction" refers to the width of a fabric in a direction generally perpendicular to the direction in which it is produced, as opposed to "machine direction" which refers to the length of a fabric in the direction in which it is produced.

"Cycle" and "cycling" refer to a process of repeatedly stretching and retracting a material to either test material properties or to activate latent material properties.

"Elastic," "elasticized" and "elasticity" mean that property of a material or composite by virtue of which it tends to recover its original size and shape after removal of a force causing a deformation.

"Elastomeric" refers to a material or composite which can be elongated by at least 50 percent of its relaxed length and which will recover, upon release of the applied force, at least 40 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Film" refers to a thermoplastic film made using a film extrusion and/or foaming process, such as a cast film or blown film extrusion process. For the purposes of the present invention, the term includes breathable microporous films that act as liquid barriers.

"Layer" when used in the singular can have the dual meaning of a single element or a plurality of elements.

"Liquid permeable material" or "liquid water-permeable material" refers to a material present in one or more layers, such as a film, nonwoven fabric, or open-celled foam, which is porous, and which is permeable to the flow of water and other aqueous liquids through the pores or openings. The pores or openings in the film or foam, or spaces between fibers or filaments in a nonwoven web, are large enough and frequent enough to permit leakage and flow of liquid water through the material.

"Machine direction" refers to the length of a fabric in the direction in which it is produced, as opposed to "cross direction" which refers to the width of a fabric in a direction generally perpendicular to the machine direction.

"Meltblown fiber" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter the meltblown fibers carried by the high velocity gas stream are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

"Nonwoven" and "nonwoven web" refer to fibrous materials and webs of fibrous material which are formed without the aid of a textile weaving or knitting process.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the molecules. These configurations include, but are not limited to isotactic, syndiotactic and atactic symmetries.

"Selectively stretched" refers to stretching certain regions of a material to a greater extent than other regions of the material. The selection of the regions to be stretched to a greater extent can be strategically planned based on a desired level of breathability in those regions of the material, with the regions stretched to a greater extent having higher breathability than the regions stretched to a lesser extent.

"Spunbonded fiber" refers to small diameter fibers which are formed by extruding molten thermoplastic material as filaments from a plurality of fine capillaries of a spinnerette having a circular or other configuration, with the diameter of the extruded filaments then being rapidly reduced as described, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally are not tacky when they are deposited onto a collecting surface. Spunbond fibers are generally continuous and often have average deniers larger than about 0.3, more particularly, between about 0.6 and 10.

"Stretchable" means that a material can be stretched, without breaking, by at least 50% (to at least 150% of its initial unstretched length) in at least one direction, suitably by at least 100% (to at least 200% of its initial length), desirably by at least 150% (to at least 250% of its initial length). The term includes elastic materials as well as materials that stretch but do not significantly retract.

"Superabsorbent" or "superabsorbent material" refers to a water-swellable, water-insoluble organic or inorganic material capable, under the most favorable conditions, of absorbing at least about 15 times its weight and, more desirably, at least about 30 times its weight of an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

"Thermoplastic" describes a material that softens when exposed to heat and which substantially returns to a non-softened condition when cooled to room temperature.

These terms may be defined with additional language in the remaining portions of the specification.

DETAILED DESCRIPTION OF THE PRESENTLY PREFERRED EMBODIMENTS

The present invention is directed to a stretchable, breathable laminate having targeted zones of higher breathability. The material of the present invention is particularly suitable for use as an outer cover for disposable absorbent articles. Examples of such suitable articles include diapers, training pants, incontinence products, swim wear, other personal care or health care garments, or the like.

Referring to FIG. 1, there is shown a cross-sectional view of a breathable laminate 40. The laminate 40 is made up of a breathable, microporous, elastic film 32 and a nonwoven facing material 12 bonded to the film 32. The breathability of the laminate 40, expressed as water vapor transmission rate (WVTR), is essentially equal to the breathability of the film layer 32 when the film 32 and the facing material 12 are initially bonded. The WVTR is a function of both film thickness and film composition. The film layer 32 suitably can deliver moderate breathability, expressed as WVTR, in a range of about 500 to 30,000 grams/m$^2$-24 hours using the Mocon WVTR test procedure described below. Suitably, the moderate WVTR of the film layer 32 is at least about 500 grams/m$^2$-24 hours, even more suitably at least about 750 grams/m$^2$-24 hours, most suitably at least about 1000 grams/m$^2$-24 hours. After the film 32 and the facing material 12 are bonded, the laminate 40 can be stretched in some or all areas of the laminate 40 to impart higher breathability in the stretched zones. A zone of higher breathability is defined as having a WVTR at least 10% higher than an adjacent zone of moderate breathability.

The film 32 is suitably a microporous film which includes an amorphous polymer 42 and filler particles 44. The filler particles 44 in the film 32 initiate the formation of voids surrounding the particles upon stretching of the film 32. The voids impart breathability to the film 32 by creating a tortuous path of thin membranes through which water vapor, but not liquid water, can pass. Hence, the laminate 40, including the film 32 and the facing layer 12 bonded together, can be differentially stretched to obtain zones of different breathability. Examples of microporous films are described in U.S. Pat. No. 5,695,868 issued to McCormack, U.S. Pat. No. 5,932,497 issued to Morman, et al., U.S. Pat. No. 6,045,900 issued to Haffner, et al., and U.S. Pat. No. 6,072,005 issued to Kobylivker, et al., all of which are hereby incorporated by reference.

The film polymer 42 may be a low density ethylene elastomer which includes ethylene copolymers having a density less than about 0.90 grams/cm$^3$, desirably from about 0.86 grams/cm$^3$ to about 0.89 grams/cm$^3$ and even more desirably from about 0.87 grams/cm$^3$ to about 0.88 grams/cm$^3$. Suitably, the ethylene elastomers include linear low density polyethylene. The ethylene elastomer suitably includes at least about 50% by weight of the polymeric portion 42 of the film 32, and more suitably from about 70% to 100% by weight. Suitably, the ethylene elastomer includes a polymer wherein the ethylene monomers are polymerized with an alpha-olefin such that the resulting polymer composition has a narrow molecular weight distribution ($M_w/M_n$) of about 2, homogeneous branching, and controlled long chain branching. Suitable alpha-olefins include, but are not limited to, 1-octene, 1-butene, 1-hexene and 4-methyl-pentene. Exemplary polymers include those made by "metallocene," "constrained geometry" or "single-site" catalysts such as those described in U.S. Pat. No. 5,472,775 to Obijeski, et al. U.S. Pat. No. 5,451,450 to Erderly, et al.; U.S. Pat. No. 5,204,429 to Kaminsky, et al.; U.S. Pat. No. 5,539,124 to Etherton, et al.; and U.S. Pat. No. 5,554,775 to Krishnamurti, et al.; each of which is hereby incorporated by reference.

The metallocene process generally uses a metallocene catalyst which is activated, i.e., ionized, by a co-catalyst. Examples of metallocene catalysts include bis(n-butylcyclopentadienyl)titanium dichloride, bis(n-butylcyclopentadienyl) zirconium dichloride, bis(cyclopentadienyl)scandium chloride, bis(indenyl)zirconium dichloride, bis(methylcyclopentadienyl)titanium dichloride, bis(methylcyclopentadienyl)zirconium dichloride, cobaltocene, cyclopentadienyltitanium trichloride, ferrocene, hafnocene dichloride, isopropyl(cyclopentadienyl,-1-fluorenyl)zirconium dichloride, molybdocene dichloride, nickelocene, niobocene dichloride, ruthenocene, titanocene dichloride, zirconocene chloride hydride, zirconocene dichloride, among others. A more exhaustive list of such compounds is included in U.S. Pat. No. 5,374,696 to Rosen, et al. and assigned to the Dow Chemical Company. Numerous other metallocene, single-site and/or similar catalyst systems are known in the art.

Regarding metallocene based elastomeric polymers, U.S. Pat. No. 5,204,429 to Kaminsky, et al. describes a process which may produce elastic copolymers from cycloolefins and linear olefins using a catalyst which is a stereorigid chiral metallocene transition metal compound and an aluminoxane. The polymerization is carried out in an inert solvent such as an aliphatic or cycloaliphatic hydrocarbon such as toluene. U.S. Pat. Nos. 5,278,272 and 5,272,236, both to Lai, et al., describe polymers having particular elastic properties, and are both hereby incorporated by reference. Suitable low density ethylene elastomers are commercially available from Dow Chemical Company of Midland, Mich., under the trade name AFFINITY™, including AFFINITY™ EG8200 (5 MI, 0.870 grams/cm$^3$), XU 58200.02 (30 MI, 0.870 grams/cm$^3$), XU 58300.00 (10 MI, 0.870 grams/cm$^3$) and from Exxon Mobil Chemical Co. of Houston, Tex., under the trade name EXACT™ 4049 (4.5 MI, 0.873 grams/cm$^3$); 4011 (2.2 MI, 0.888 grams/cm$^3$); 4041 (3 MI, 0.878 grams/cm$^3$); 4006 (10 MI, 0.88 grams/cm$^3$).

In addition to the amorphous polymer, the polymeric component 42 of the film layer 32 may further include up to about 50% by weight of one or more additional polymers. The film layer 32 may thus also include additional thermoplastic polymers, suitably polyolefins and even more suitably blends and/or copolymers of ethylene and/or propylene. Exemplary polymers include, but are not limited to, polyethylene (homopolymer), linear low density polyethylene (having a density of 0.900–0.935 grams/cm$^3$), ethylene vinyl acetate (EVA), ethylene methyl acrylate (EMA), ethylene normal butyl acrylate (EnBA), flexible polyolefins and/or ethylene-propylene copolymers. In one embodiment, the very low density ethylene elastomer is blended with a second low or medium density polyethylene polymer or copolymer having a density ranging from about 0.90 to about 0.95 grams/cm$^3$. Additional commercially available polyolefin polymer components include, but are not limited to Montell Catalloy Polymer KS350, KS357 and KS359 available from Montell North America, Inc. Montell Catalloy polymer is an olefinic multistep reactor product wherein an amorphous ethylene propylene random copolymer is molecularly dispersed in a predominantly semicrystalline high % propylene monomer/low % ethylene monomer continuous matrix, an example of which is described in U.S. Pat. No. 5,300,365 to Ogale.

The breathable elastic film 32 should not be so thick as to substantially impair its water vapor transmission. For water vapor permeable films the relationship between the WVTR of the films and the thickness of the films may vary due to the affinity of water to the films. Stretched film compositions having somewhat lower water-vapor permeability than the ranges listed should therefore be made into thinner films in order to achieve suitable vapor transmission. For instance, the vapor permeable stretched film composition may be less than about 25.4 micrometers thick, or less than about 12.7 micrometers thick, or less than about 7.62 micrometers thick depending on the strength of the film and the water vapor permeability of the composition.

As mentioned, the filler particles 44 in the film 32 initiate the formation of voids that impart breathability to the film 32 upon stretching. The film 32 may be uniaxially or biaxially stretched. The film 32 is at least minimally stretched to impart breathability to the entire film 32 prior to applying differential, selective stretching. The film 32 may be uniaxially stretched to about 1.1–7.0 times its original length, preferably to about 1.5–6.0 times its original length, most preferably to about 2.5–5.0 times its original length. The film 32 may alternatively be biaxially stretched using conventional techniques familiar to persons skilled in the art.

The film 32 can be initially uniformly stretched to impart a moderate level of breathability across the film 32. In accordance with the invention, the film 32 is further selectively stretched in one or more regions to impart higher breathability to those regions. The selective stretching can be in the same direction as the initial stretching, or can be in a different direction. For instance, the initial stretching and selective further stretching can both be in the machine direction, or one can be in the machine direction and the other in the cross direction.

Advantageously, the film 32 may be initially stretched using an elevated stretch temperature of about 150–200° F. for most polyolefin-based films. The elevated stretch temperature can be sustained by heating some of the rollers 28, 30. The optimum stretch temperature varies with the type of matrix polymer in the film 32, and is always below the melting temperature of the matrix polymer. The film 32 may also be heated during the subsequent selective stretching, but non-heated selective stretching is preferred.

As used herein, a "filler" is meant to include particulates and/or other forms of materials which can be added to the polymer blend prior to film extrusion, and which will not chemically interfere with or adversely affect the extruded film and, further, which can be uniformly dispersed throughout the film. Generally the fillers 44 will be in particulate form with average particle sizes in the range of about 0.1 to about 7 micrometers, desirably from about 0.1 to about 4 micrometers. As used herein the term "particle size" describes the largest dimension or length of the filler 44. Both organic and inorganic fillers are contemplated for use with the present invention provided they do not interfere with the film forming process and/or subsequent laminating processes. Examples of fillers 44 include calcium carbonate ($CaCO_3$), various clays, silica ($SiO_2$), alumina, barium sulfate, talc, magnesium sulfate, titanium dioxide, zeolites, aluminum sulfate, cellulosic powders, diatomaceous earth, gypsum, magnesium carbonate, barium carbonate, kaolin, mica, carbon, magnesium oxide, aluminum hydroxide, pulp powder, wood powder, cellulose derivatives, polymeric particles, chitin and chitin derivatives. The filler particles optionally may be coated with a fatty acid, such as stearic acid or behenic acid, and/or other material in order to facilitate the free flow of the particles (in bulk) and their ease of dispersion into the polymer. The filled film 32 will usually contain at least about 35% filler 44 based upon the total weight of the film layer, more desirably from about 45% to about 65% by weight.

The film 32, prior to stretching, suitably has a basis weight of less than about 100 grams per square meter ($g/m^2$) and even more suitably less than about 60 $g/m^2$. Upon stretching, the film 32 suitably has a basis weight of less than 60 $g/m^2$, and even more suitably between about 15 and 35 $g/m^2$. Typically, such lower basis weight films have a thickness of about 15 micrometers to about 30 micrometers.

The nonwoven facing material 12 may be a spunbond web and may be formed by known spunbonding processes. The nonwoven material 12 may also be a meltblown web, an air-laid web, a bonded-carded web, or a laminate of two or more nonwoven layers. The nonwoven material 12 may be rendered extensible as explained below. The nonwoven facing material 12 provides a cloth-like feel and appearance on the laminate 40 of the invention.

The facing material 12 can be a nonwoven web necked in the machine direction, thereby imparting cross directional stretch to the material. The process of necking is described in U.S. Pat. No. 5,226,992 issued to Morman, hereby incorporated by reference. The necked material 12 can be bonded at multiple spaced-apart locations to the elastic film 32. After the necked material 12 and the film 32 are bonded, the resulting composite 40 yields cross-directional elasticity.

Figure 2:
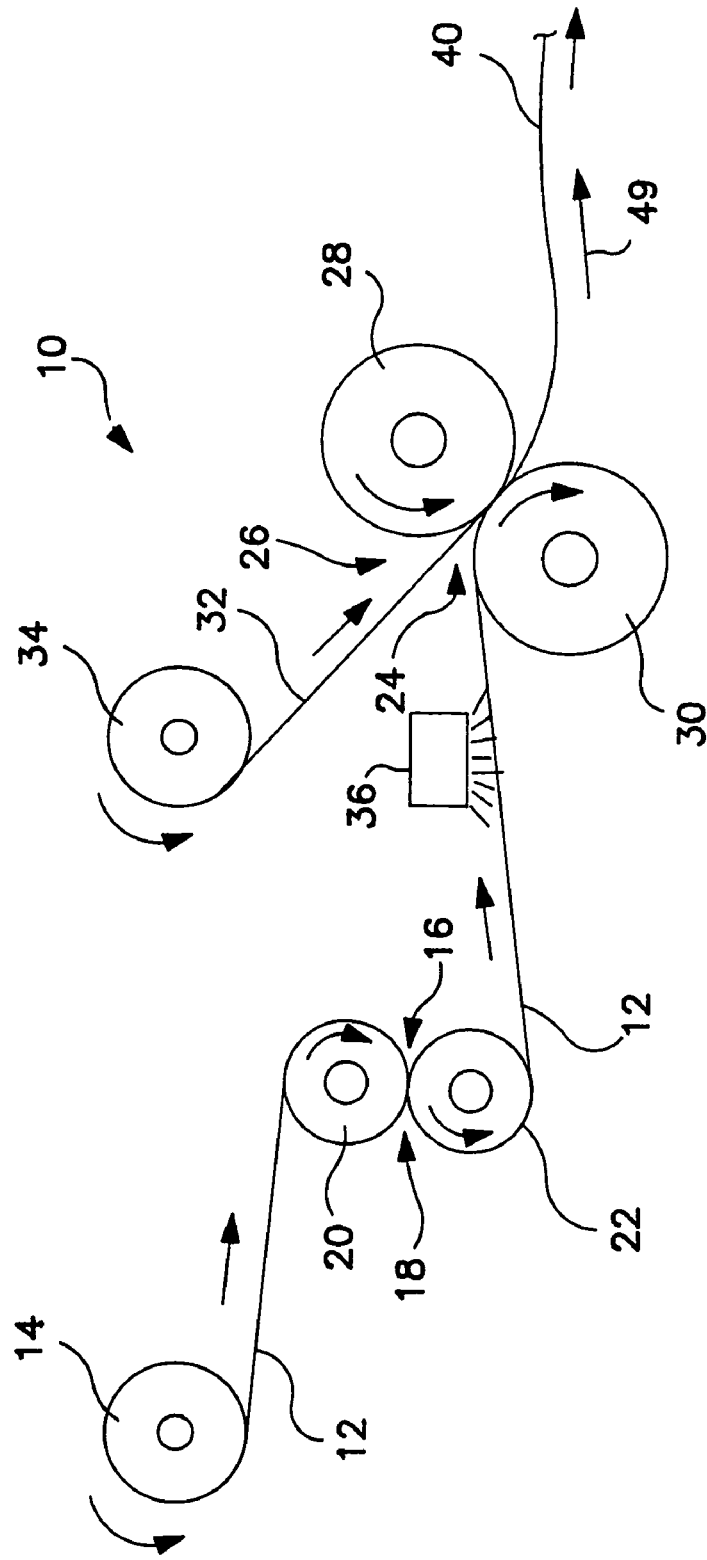
FIG. 2 is a schematic representation of an exemplary process for forming a composite breathable laminate with enhanced breathability.
Figure 3:
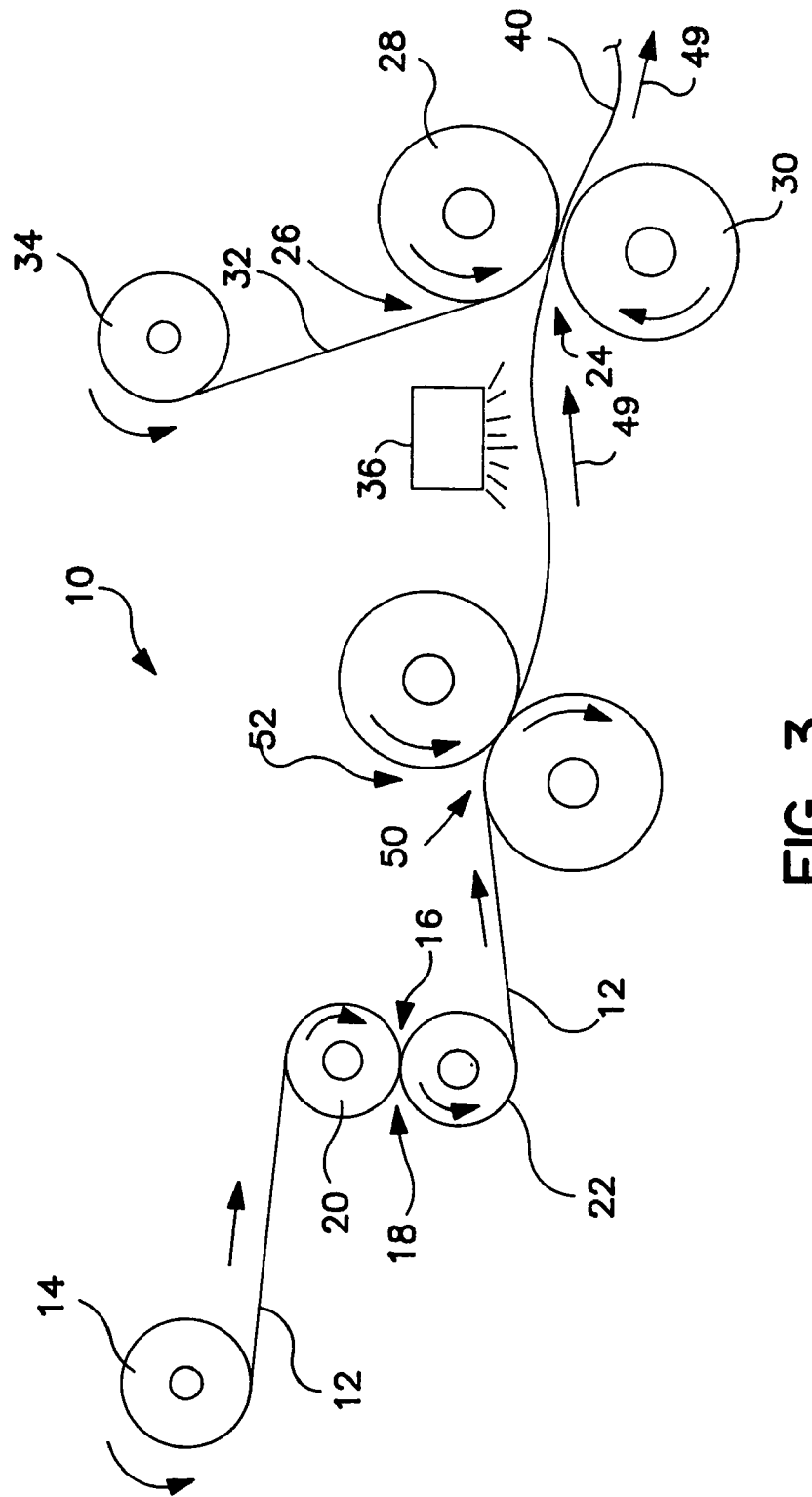
FIG. 3 is another schematic of an exemplary process for forming a composite breathable laminate with enhanced breathability.

The term "cross direction," as used herein, refers to the width of a material in a direction generally perpendicular to the direction in which it is produced, as opposed to "machine direction," which refers to the length of a material in the direction in which it is produced. For reference, arrow 49 depicts the machine direction in FIGS. 2 and 3, while the cross direction in FIGS. 2 and 3 is essentially perpendicular to the plane of the figures thereby extending into and out of the page. Arrow 48 depicts the cross direction and arrow 49 depicts the machine direction in FIG. 4.

If the nonwoven facing material 12 is necked, fibers of the material 12 should be joined by interfiber bonding to form a coherent web structure which is able to withstand necking. Interfiber bonding may be produced by entanglement between individual meltblown fibers. The fiber entangling is inherent in the meltblown process but may be generated or increased by processes such as, for example, hydraulic entangling or needlepunching. Alternatively and/or additionally a bonding agent may be used to increase the desired bonding. A spunbond web has interfiber bonding caused by thermal bonding of the fibers in the spunbonding process.

The facing material 12 can be elastic in nature, for example, as a spunbond nonwoven produced from a thermoplastic elastomer creating an elastic fiber matrix. Materials suitable for use in preparing an elastic facing material 12 include diblock, triblock, or multi-block elastomeric copolymers such as styrenic copolymers, including styrene-isoprene-styrene, styrene-butadiene-styrene, styrene-ethylene/butylene-styrene, or styrene-ethylene/propylene-styrene, which may be obtained from the Shell Chemical Company, under the trade designation KRATON® elastomeric resin; polyurethanes, including those available from E.I. Du Pont de Nemours Co., under the trade name LYCRA® polyurethane; polyamides, including polyether block amides available from Ato Chemical Company, under the trade name PEBAX® polyether block amide; polyesters, such as those available from E.I. Du Pont de Nemours Co., under the trade name HYTREL® polyester; and single-site or metallocene-catalyzed polyolefins having density less than about 0.89 grams/$cm^3$, available from Dow Chemical Co. under the trade name AFFINITY®, also available from Exxon Mobil Chemical Co. under the trade name EXACT™.

A number of block copolymers can be used to prepare the elastic facing material 12 useful in this invention. Such block copolymers generally include an elastomeric midblock portion and a crystalline or amorphous endblock portion. The block copolymers used in this invention generally have a three-dimensional physical crosslinked structure below the endblock portion's glass transition temperature ($T_g$) and are therefore elastomeric. The block copolymers are also thermoplastic in the sense that they can be melted, formed, and re-solidified several times with little or no change in physical properties (assuming a minimum of oxidative degradation).

Several different methods can be used to synthesize block copolymers. For example, a couple of methods are described on pages 52–53 and 199–200 in the book *Thermoplastic Elastomers, A Comprehensive Review*, edited by N. R. Legge, et al., published by Hanser Publishers, New York. More particularly, one way of synthesizing such block copolymers is to polymerize the crystalline endblock portions separately from the elastomeric midblock portions. Once the midblock and endblock portions have been separately formed, they can be linked. Typically, midblock portions can be obtained by polymerizing di- and tri-unsaturated $C_4$–$C_{10}$ hydrocarbons such as, for example, dienes such as butadiene, isoprene, and the like, and trienes such as 1, 3, 5-heptatriene, and the like. When an endblock portion A is joined to a midblock portion B, an A-B block copolymer unit is formed, which unit can be coupled by various techniques or with various coupling agents C to provide a structure such as A-B-A, which is believed to include two A-B blocks joined together in a tail-to-tail A-B-C-B-A arrangement. By a similar technique, a radial block copolymer can be formed having the formula $(A-B)_n C$, wherein C is the hub or central polyfunctional coupling agent and n is a number greater than 2. Using the coupling agent technique, the functionality of C determines the number of A-B branches.

Endblock portion A generally includes a poly(vinylarene), such as polystyrene, having an average molecular weight between 1,000 and 60,000. Midblock portion B generally includes a substantially amorphous polyolefin such as polyisoprene, ethylene/propylene polymers, ethylene/butylene polymers, polybutadiene, and the like, or mixtures thereof, having an average molecular weight between about 5,000 and about 450,000. The total molecular weight of the block copolymer is suitably about 10,000 to about 500,000 and more suitably about 200,000 to about 300,000. Any residual unsaturation in the midblock portion of the block copolymer can be hydrogenated selectively so that the content of olefinic double bonds in the block copolymers can be reduced to a residual proportion of less than 5 percent and suitably less than about 2 percent. Such hydrogenation tends to reduce sensitivity to oxidative degradation and may have beneficial effects upon elastic properties.

Suitable block copolymers used in this invention include at least two substantially polystyrene endblock portions and at least one substantially ethylene/butylene mid-block portion. As an example, ethylene/butylene typically may include the major amount of the repeating units in such a block copolymer and can constitute, for example, 70 weight-percent or more of the block copolymer. The block copolymer can have three or more arms, and good results can be obtained with, for example, four, five, or six arms. The midblock portion can be hydrogenated, if desired.

Linear block copolymers, such as A-B-A, A-B-A-B-A or the like, are suitably selected on the basis of endblock content, large endblocks being preferred. For polystyrene-ethylene/butylene-polystyrene block copolymers, a styrene content in excess of about 10 weight-percent is suitable, such as between about 12 to about 30 weight-percent. With higher styrene content, the polystyrene endblock portions generally have a relatively high molecular weight. A commercially available example of such a linear block copolymer is a styrene-ethylene/butylene-styrene block copolymer which contains about 13 weight-percent styrene units and essentially the balance being ethylene/butylene units, commercially available from the Shell Chemical Company, under the trade designation KRATON® G1657 elastomer. Typical properties of KRATON® G1657 elastomer are reported to include a tensile strength of 3400 pounds per square inch ($2 \times 10^6$ kilograms per square meter), a 300-percent modulus of 350 pounds per square inch ($1.4 \times 10^5$ kilograms per square meter), an elongation of 750 percent at break, a Shore A hardness of 65, and a Brookfield viscosity, when at a concentration of 25 weight-percent in a toluene solution, of about 4200 centipoise at room temperature. Another suitable elastomer, KRATON® G2740, is a styrene ethylene/butylene block copolymer blended with tackifier and low density polyethylene.

Other suitable elastomeric polymers may also be used to make the facing material 12. These include, without limitation, elastomeric (single-site or metallocene catalyzed) polypropylene, polyethylene and other alpha-olefin homopolymers and copolymers, having density less than about 0.89 grams/cm$^3$; ethylene vinyl acetate copolymers; and substantially amorphous copolymers and terpolymers of ethylene-propylene, butene-propylene, and ethylene-propylene-butene.

The elastomeric fibers may be substantially continuous or staple-length, but are preferably substantially continuous. The elastomeric fibers may be produced using a spunbonding process, a meltblowing process, or other suitable processes. The elastomeric fibers may have average diameters of about 1 to 75 micrometers, preferably about 1 to 40 micrometers, more preferably about 1 to 30 micrometers.

The facing material 12 may also be a composite material made of a mixture of two or more different fibers or a mixture of fibers and particulates. Such mixtures may be formed by adding fibers and/or particulates to the gas stream in which meltblown fibers are carried so that an intimately entangled commingling of meltblown fibers and other materials, e.g., wood pulp, staple fibers and particulates such as, for example, hydrocolloid (hydrogel) particulates commonly referred to as superabsorbent materials, occurs prior to collection of the meltblown fibers upon a collecting device to form a coherent web of randomly dispersed meltblown fibers and other materials, such as disclosed in U.S. Pat. No. 4,100,324, the disclosure of which is hereby incorporated by reference.

Referring to FIG. 2, schematically illustrated at 10 is a process for forming a stretchable, breathable laminate 40 with enhanced breathability. A nonwoven facing material 12 is unwound from a supply roll 14 and travels in the direction indicated by the arrow associated therewith as the supply roll 14 rotates in the direction of the arrows associated therewith. The nonwoven facing material 12 passes through a nip 16 of the drive roller arrangement 18 formed by the drive rollers 20 and 22, and then toward a nip 24 of the bonder roller arrangement 26 formed by the bonder rollers 28, 30 where the material 12 meets and is bonded to a breathable, microporous, elastic film 32. Alternatively, the material 12 may be passed, directly in-line with its forming process, through the nip 16 without first being stored on a supply roll.

The breathable, microporous, elastic film 32 is unwound from a supply roll 34 and travels in the direction indicated by the arrow associated therewith as the supply roll 34 rotates in the direction of the arrows associated therewith. The breathable elastic film 32 passes through the nip 24 of the bonder roller arrangement 26 formed by the bonder rollers 28 and 30. The breathable elastic film 32 may also be passed directly through the nip 24 without first being stored on a supply roll. The elastic film 32 may be stretched in one direction (e.g. the machine direction) prior to bonding to the nonwoven material 12, as explained below.

A bonding device 36 applies a bonding material, such as a spray adhesive, onto the facing material 12 at multiple, spaced apart locations, as the material 12 and the film 32 approach the nip 24 of the bonder roller arrangement 26. Thus, once the facing material 12 and the breathable elastic film 32 are nipped together in the bonder roller arrangement 26, a stretchable, breathable laminate 40 is formed.

Breathability in the stretched zones is increased due to the nature of the microporous film 32, which, as mentioned, acquires increased breathability upon stretching. The differential stretching of the laminate 40 may be carried out prior to incorporation of the laminate 40 into a final product, such as an absorbent article. The zones of high breathability are suitably intended for parts of products within close proximity to regions or segments that become saturated with liquid. For example, the crotch region in the outer cover of a diaper is a region that tends to become saturated with liquid. Therefore, having zones of high breathability in the front and back areas of the diaper would allow the liquid vapor from the saturated crotch region to escape through the outer cover.

Alternatively, rather than stretching the laminate 40 prior to incorporation into an end product, the laminate 40 can be used in areas of products that will be stretched, thereby letting the laminate-stretching step of the manufacturing process be carried out by the wearer, or a care-giver applying the product to the wearer. For example, an outer cover of a diaper made of the laminate 40 of the invention can have a relatively narrow front and a relatively narrow back, such that the person applying the garment must stretch the front and the back in order to apply the garment to the wearer. As a result of the stretching, the front and the back of the garment achieve greater breathability than the crotch region.

Alternatively, the differential stretching of laminate 40 may be carried out simultaneously with the manufacture of the absorbent article.

In the process 10 shown in FIG. 3, the facing material 12 passes through the nip 16 of the S-roll arrangement 18 in a reverse S-path as indicated by the rotation direction arrows associated with the stack rollers 20 and 22. From the S-roll arrangement 18, the facing material 12 passes through a pressure nip 50 formed by a neck roller arrangement 52. The peripheral linear speed of the rollers of the S-roll arrangement 18 can be controlled to be less than the peripheral linear speed of the rollers of the neck roller arrangement 52, such that the facing material 12 is tensioned between the S-roll arrangement 18 and the pressure nip of the neck roll arrangement 52. By adjusting the difference in the speeds of the rollers, the facing material 12 can be tensioned so that it necks a desired amount. The facing material 12 having mechanically manipulated cross direction stretchability attributable to the necking is then adhesively or thermally joined to the breathable elastic film 32 during their passage through a bonder roller arrangement 26 to form a stretchable, breathable laminate 40. Breathability of the laminate 40, or zones of the laminate 40, can be enhanced by stretching the laminate with a stretching device (not shown).

The facing material 12 component of the laminate 40 is typically open and porous, and does not significantly affect the breathability of the laminate 40. In other words, the moisture breathability of the film 32 should determine the breathability of the laminate 40. However, care should be taken to bond the film 32 and facing material 12 together using techniques that do not significantly disrupt the breathability of the laminate 40. If an adhesive is used, the adhesive should cover only a portion of the total film area, and should be applied as thinly as possible. The preferred adhesive for attaching polyurethane films to a spunbonded web, for example, is a reactive polyurethane-based adhesive available from Shawmut Mills in Bridgewater, Mass. When used, an adhesive should be applied at a basis weight less than about 5.0 grams per square meter (gsm). The adhesive should suitably cover not more than about 75% of the film surface unless the adhesive itself is very water-vapor permeable. Furthermore, any type of bonding that is used, whether it is adhesive, thermal, or any other type, the bonding is suitably discontinuous, thereby bonding the facing material 12 to the film 32 in multiple, spaced-apart locations. The discontinuous bonding does not inhibit or restrict simultaneous movement of the layers the way continuous bonding does, particularly when the film 32 is elastomeric and the facing material 12 is stretchable but does not retract on its own. However, for a given combination of materials, and in view of the herein contained disclosure, the processing conditions necessary to achieve satisfactory bonding can be readily determined by one of skill in the art.

Conventional drive-means and other conventional devices which may be utilized in conjunction with the apparatus of FIGS. 2 and 3 are well known and, for purposes of clarity, have not been illustrated in the schematic views of FIGS. 2 and 3.

Figure 4:
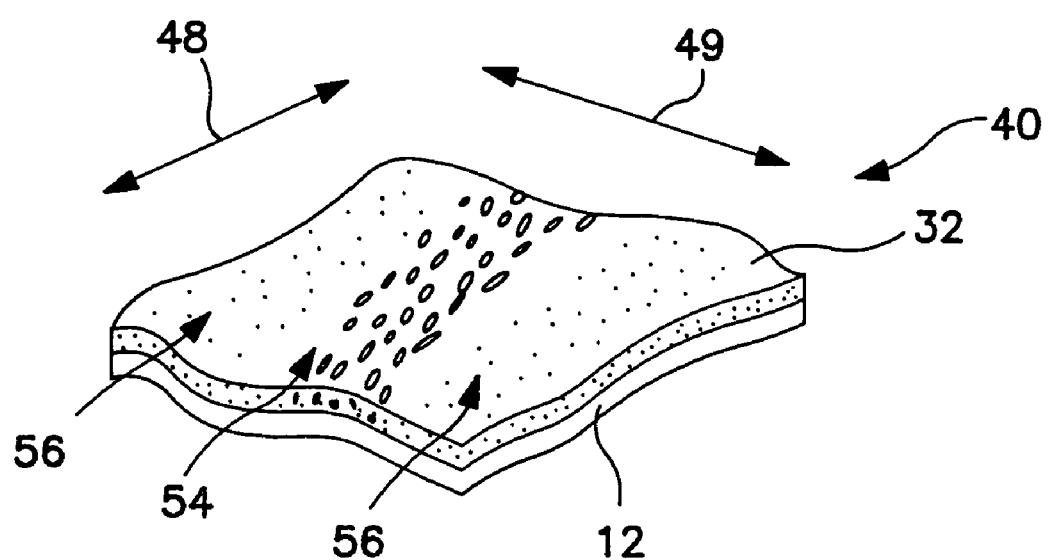
FIG. 4 is a perspective view of a breathable laminate of the present invention.

A perspective view of a stretchable, breathable laminate 40 with selectively enhanced breathability is shown in FIG. 4. Suitably, at least one zone of "higher breathability" is created among the zone or zones of "moderate breathability". The zones of moderate breathability 56 have a WVTR considerably lower than the WVTR of the zones of higher breathability 54. Suitably, the zones of moderate breathability 56 have a WVTR not greater than the WVTR of the film layer 32 before lamination. The zones of higher breathability 54 are zones that have been further stretched by a stretching device (not shown) after the laminate 40 has been formed. These zones of higher breathability 54 suitably have a WVTR at least 10% higher than the WVTR of the zones of moderate breathability 56. More suitably the WVTR of the zones of higher breathability 54 are at least 30% higher than the WVTR of the zones of moderate breathability 56. Most suitably, the WVTR of the zones of higher breathability 54 are at least 50% higher than the WVTR of the zones of moderate breathability 56.

Suitably, the breathable laminate 40 of the invention can stretch between about 50% and 200% in the cross direction, more suitably between about 70% and 170%, most suitably between about 100% and 150%. Similarly, when a facing material 12 having machine direction stretchability is used to make the laminate 40, the stretchability of the laminate 40 in the machine direction is suitably between about 50% and 200% in the machine direction, more suitably between about 70% and 170%, most suitably between about 100% and 150%. The laminate 40 suitably recovers at least 40% of its elongation upon retraction in the cross direction and also in the machine direction if an elastomeric facing material 12 is used, more suitably at least 50% of its elongation is recovered, and desirably not more than 75% of the elongation is recovered. If the elongation totally recovers, the breathability may be impeded by closing of the micropores. Elastic tension capabilities of the laminates are generally determined by the type and basis weight of the film components, however, the facing type and lamination method can impact tension properties, permanent set and hysteresis properties of the resulting laminate 40. As a result, machine direction and cross direction properties can be altered by the type of facing and lamination technique used.

Figure 5:
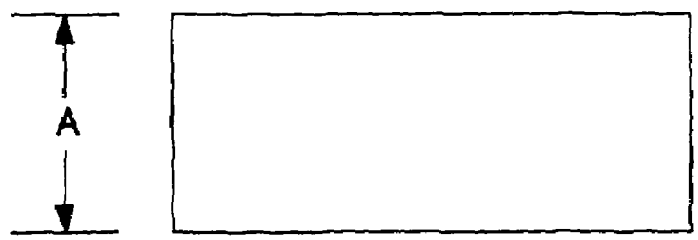
FIG. 5 is a representative plan view of an exemplary facing material before tensioning and necking.
Figure 6:
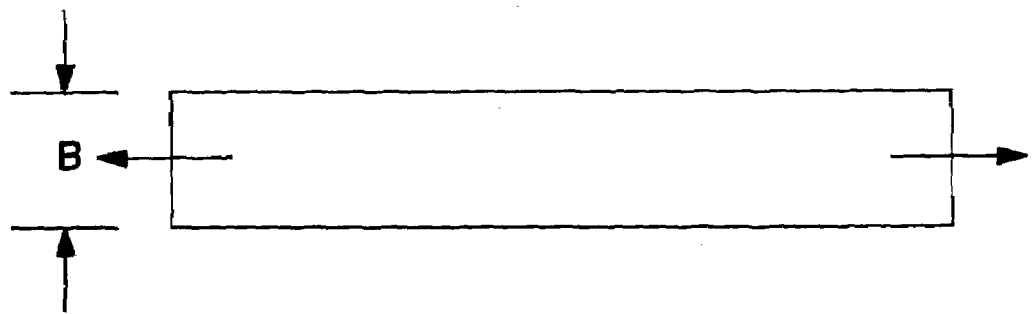
FIG. 6 is a plan view of an exemplary facing material necked in a machine direction.
Figure 7:
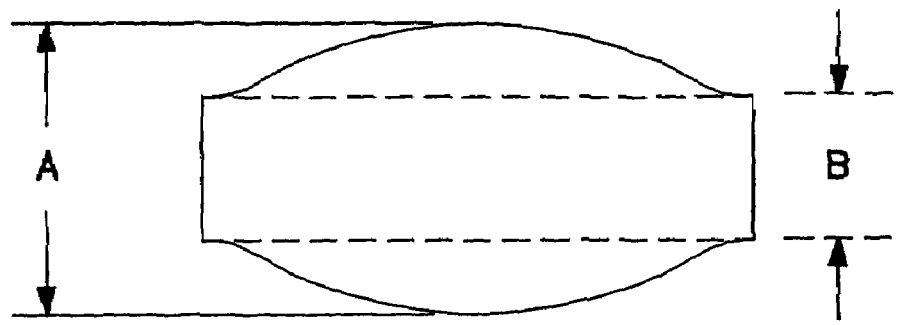
FIG. 7 is a plan view of an exemplary composite material while partially stretched in the cross direction.

For example, with reference to FIGS. 5, 6 and 7, if it is desired to prepare a composite breathable laminate that is stretchable to at least 150% elongation, a width of neckable material shown schematically and not necessarily to scale in FIG. 5 having a width "A" such as, for example, 250 cm, is tensioned so that it necks down to a width "B" of about 100 cm. The necked material shown in FIG. 6 is then joined to an elastic sheet (not shown) having a width of approximately 100 cm and which is at least stretchable to a width of 250 cm. The resulting composite elastic necked-bonded material shown schematically and not necessarily to scale in FIG. 7 has a width "B" of about 100 cm and is stretchable to at least the original 250 cm width "A" of the neckable material for an elongation of about 150%. As can be seen from the example, the elastic limit of the elastic sheet needs only to be as great as the minimum desired elastic limit of the composite elastic necked-bonded material.

For the following examples, four different combinations of breathable, microporous films and nonwoven facing materials were laminated and stretched in laminate form, resulting in laminates in accordance with the present invention. The composition of the laminates is shown in Table 1.

TABLE 1

Composition of Cycled Laminates

| Sample | Film | Resin | Stabilizer | CaCO$_3$ | Film Basis Weight (grams/m$^2$) | Spunbond Necking Level |
|---|---|---|---|---|---|---|
| 1 | XSF-638 | 8200*/1845** | E 17 | 55% Omya | 60 | 45% |
| 2 | XSF-638 | 8200*/1845** | E 17 | 55% Omya | 100 | 35% |
| 3 | XSF-638 | 8200*/1845** | E 17 | 55% Omya | 100 | 60% |
| 4 | XSF-638 | 8200*/1845** | E 17 | 55% Omya | 100 | 45% |

*8200 is AFFINITY ® EG8200, 0.870 g/cc
**1845 is AFFINITY ® PL 1845, 0.910 g/cc

Each of the film layers was adhesively bonded to the corresponding facing material using REXTAC™ 2730 adhesive from Huntsman. Once the laminates were formed, each laminate was cycled. The breathability of each laminate, both prior to and after cycling, is shown in Table 2.

Cycling was carried out using a constant-rate-of-extension tensile tester, designated as Sintech 2, Model 3397-139, available from Sintech Corporation, Cary, N.C. Each laminate test sample was approximately 4.5 inches by 3 inches, with the 4.5 inch side being in the cross direction. Each 3-inch wide specimen was clamped by two pneumatic jaws so that the gauge length (jaw separation) was 2 inches, and the direction of pull was in the cross direction. The pulling speed was set at 500 mm/min. Testing was done throughout four extension/retraction cycles, during which the specimen was first pulled to 100% elongation (4-inch jaw separation), the jaws then stopped and immediately returned to the starting gauge length, then three more extension-retraction cycles were repeated. Breathability of each sample was measured, both before and after cycling, using the Mocon WVTR test procedure described below.

TABLE 2

Breathability of Cycled Laminates

| Sample | Initial WVTR (grams/m$^2$ - 24 hours) | Post-Cycling WVTR (grams/m$^2$ - 24 hours) |
|---|---|---|
| 1 | 1787 | 3055 |
| 2 | 1855 | 2880 |
| 3 | 1180 | 2730 |
| 4 | 603 | 2587 |

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

Test Procedure for Water Vapor Transmission Rate (WVTR)

A suitable technique for determining the WVTR (water vapor transmission rate) value of a film or laminate material of the invention is the test procedure standardized by INDA (Association of the Nonwoven Fabrics Industry), number IST-70.4-99, entitled "STANDARD TEST METHOD FOR WATER VAPOR TRANSMISSION RATE THROUGH NONWOVEN AND PLASTIC FILM USING A GUARD FILM AND VAPOR PRESSURE SENSOR" which is incorporated by reference herein. The INDA procedure provides for the determination of WVTR, the permeance of the film to water vapor and, for homogeneous materials, water vapor permeability coefficient.

The INDA test method is well known and will not be set forth in detail herein. However, the test procedure is summarized as follows. A dry chamber is separated from a wet chamber of known temperature and humidity by a permanent guard film and the sample material to be tested. The purpose of the guard film is to define a definite air gap and to quiet or still the air in the air gap while the air gap is characterized. The dry chamber, guard film, and the wet chamber make up a diffusion cell in which the test film is sealed. The sample holder is known as the Permatran-W Model 100K manufactured by Mocon/Modern Controls, Inc., Minneapolis, Minn. A first test is made of the WVTR of the guard film and the air gap between an evaporator assembly that generates 100% relative humidity. Water vapor diffuses through the air gap and the guard film and then mixes with a dry gas flow which is proportional to water vapor concentration. A sensor generates a signal proportional to the vapor content of the gas stream. The electrical signal is routed to a computer for processing. The computer calculates the transmission rate of the air gap and the guard film and stores the value for further use.

The transmission rate of the guard film and air gap is stored in the computer as CalC. The sample material is then sealed in the test cell. Again, water vapor diffuses through the air gap to the guard film and the test material and then mixes with a dry gas flow that sweeps the test material. Also, again, this mixture is carried to the vapor sensor. The computer than calculates the transmission rate of the combination of the air gap, the guard film, and the test material. This information is then used to calculate the transmission rate at which moisture is transmitted through the test material according to the equation:

$$TR^{-1}_{test\ material} = TR^{-1}_{test\ material,\ guardfilm,\ airgap} - TR^{-1}_{guardfilm,\ airgap}$$

Calculations:
WVTR: The calculation of the WVTR uses the formula:

$$WVTR = Fp_{sat}(T)RH/Ap_{sat}(T)(1-RH))$$

where:
F=The flow of water vapor in cc/min.,
$P_{sat}(T)$=The density of water in saturated air at temperature T,
RH=The relative humidity at specified locations in the cell,
A=The cross sectional area of the cell, and,
$P_{sat}(T)$=The saturation vapor pressure of water vapor at temperature T.

We claim:

1. A breathable laminate, comprising:
a breathable, microporous, elastic film; and
a nonwoven facing material bonded to the film;
wherein the laminate is selectively stretched to form at least one stretched zone thereof resulting in zones of differential breathability comprising at least one zone of higher breathability and at least one zone of moderate breathability;
wherein the at least one stretched zone of the laminate consists of the at least one zone of higher breathability; and
wherein each of the zones of differential breathability comprises a portion of the film and a portion of the nonwoven facing material.

2. The laminate of claim 1, wherein the at least one zone of higher breathability has a water vapor transmission rate at least 10% higher than a water vapor transmission rate of the at least one zone of moderate breathability.

3. The laminate of claim 1, wherein the at least one zone of higher breathability has a water vapor transmission rate at least 30% higher than a water vapor transmission rate of the at least one zone of moderate breathability.

4. The laminate of claim 1, wherein the at least one zone of higher breathability has a water vapor transmission rate at least 50% higher than a water vapor transmission rate of the at least one zone of moderate breathability.

5. The laminate of claim 1, wherein the water vapor transmission rate of the at least one zone of moderate breathability is at least about 500 grams/$m^2$-24 hours.

6. The laminate of claim 1, wherein the water vapor transmission rate of the at least one zone of moderate breathability is at least about 750 grams/$m^2$-24 hours.

7. The laminate of claim 1, wherein the water vapor transmission rate of the at least one zone of moderate breathability is at least about 1000 grams/$m^2$-24 hours.

8. The laminate of claim 1, wherein the laminate is elastomeric.

9. The laminate of claim 1, wherein the facing material is necked.

10. The laminate of claim 1, wherein the facing material is elastomeric.

11. The laminate of claim 1, wherein the at least one selectively stretched zone is stretched at least twice.

12. The laminate of claim 1, wherein the laminate can be stretched by about 50% to about 200% in a cross direction.

13. The laminate of claim 1, wherein the laminate can be stretched by about 70% to about 170% in a cross direction.

14. The laminate of claim 1, wherein the laminate can be stretched by about 100% to about 150% in a cross direction.

15. The laminate of claim 1, wherein the laminate can be stretched by about 50% to about 200% in a machine direction.

16. The laminate of claim 1, wherein the laminate can be stretched by about 70% to about 170% in a machine direction.

17. The laminate of claim 1, wherein the laminate can be stretched by about 100% to about 150% in a cross direction.

18. An absorbent article outer cover comprising the laminate of claim 1.

19. An outer cover for absorbent articles, comprising a breathable laminate;
the breathable laminate including a breathable, microporous, elastic film and a nonwoven facing material bonded to the film;
wherein the laminate is selectively stretched to form at least one stretched zone thereof resulting in zones of differential breathability comprising at least one zone of higher breathability and at least one zone of moderate breathability;
wherein the at least one stretched zone of the laminate consists of the at least one zone of higher breathability; and
wherein each of the zones of differential breathability comprises a portion of the film and a portion of the nonwoven facing material.

20. The outer cover of claim 19, wherein the laminate is selectively stretched to form at least one stretched zone prior to incorporation in the absorbent article.

21. The outer cover of claim 19, wherein the laminate is selectively stretched to form at least one stretched zone subsequent to incorporation in the absorbent article.

22. The outer cover of claim 19, wherein the laminate is selectively stretched to form at least one stretched zone as the absorbent article is applied to a wearer.

23. The outer cover of claim 19, wherein the laminate has a water vapor transmission rate of at least about 500 grams/$m^2$-24 hours in the zone of moderate breathability.

24. The outer cover of claim 19, wherein the laminate has a water vapor transmission rate of at least about 750 grams/$m^2$-24 hours in the zone of moderate breathability.

25. The outer cover of claim 19, wherein the laminate has a water vapor transmission rate of at least about 1000 grams/$m^2$-24 hours in the zone of moderate breathability.

26. The outer cover of claim 19, wherein the facing material is necked.

27. The outer cover of claim 19, wherein the facing material is elastomeric.

28. The outer cover of claim 19, wherein the at least one selectively stretched zone is stretched at least twice.

29. A method of making an outer cover for absorbent articles, comprising the steps of:
forming a breathable laminate by bonding a nonwoven facing material to a breathable, microporous, elastic film; and
selectively stretching the breathable laminate to form at least one stretched zone thereof resulting in zones of differential breathability comprising at least one zone of higher breathability and at least one zone of moderate breathability;
wherein the at least one stretched zone of the laminate consists of the at least one zone of higher breathability; and
wherein each of the zones of differential breathability comprises a portion of the film and a portion of the nonwoven facing material.

30. The method of claim 29, further comprising the step of selectively stretching the laminate to format at least one stretched zone prior to incorporation of the laminate in the absorbent article.

31. The method of claim 29, further comprising the step of selectively stretching the laminate to form at least one stretched zone subsequent to incorporation of the laminate in the absorbent article.

32. The method of claim 29, further comprising the step of selectively stretching the laminate to form at least one stretched zone as the absorbent article is applied to a wearer.

* * * * *